United States Patent
Trouve et al.

(10) Patent No.: US 11,458,118 B2
(45) Date of Patent: Oct. 4, 2022

(54) METHODS AND PHARMACEUTICAL COMPOSITIONS FOR THE TREATMENT OF DISEASES ASSOCIATED WITH REDUCED CFTR FUNCTION

(71) Applicants: INSERM (INSTITUT NATIONAL DE LA SANTÉ ET DE LA RECHERCHE MÉDICALE), Paris (FR); UNIVERSITÉ DE BRETAGNE OCCIDENTALE, Brest (FR); ETABLISSEMENT FRANÇAIS DU SANG (EFS), La Plaine Saint Denis (FR); CENTRE HOSPITALIER REGIONAL ET UNIVERSITAIRE DE BREST, Brest (FR)

(72) Inventors: Pascal Trouve, Brest (FR); Claude Ferec, Brest (FR); Mathieu Kerbiriou, Brest (FR); Florentin Huguet, Brest (FR)

(73) Assignees: INSERM (INSTITUT NATIONAL DE LA SANTÉ ET DE LA RECHERCHE MÉDICALE), Paris (FR); UNIVERSITÉ DE BRETAGNE OCCIDENTALE, Brest (FR); ETABLISSEMENT FRANÇAIS DU SANG (EFS), La Plaine Saint Denis (FR); CENTRE HOSPITALIER REGIONAL ET UNIVERSITAIRE DE BREST, Brest (FR)

( * ) Notice: Subject to any disclaimer, the term of this patent is extended or adjusted under 35 U.S.C. 154(b) by 27 days.

(21) Appl. No.: 16/606,236

(22) PCT Filed: Apr. 20, 2018

(86) PCT No.: PCT/EP2018/060145
§ 371 (c)(1),
(2) Date: Oct. 18, 2019

(87) PCT Pub. No.: WO2018/193075
PCT Pub. Date: Oct. 25, 2018

(65) Prior Publication Data
US 2020/0121642 A1  Apr. 23, 2020

(30) Foreign Application Priority Data
Apr. 21, 2017 (EP) ................... 17305459

(51) Int. Cl.
*A61K 31/40* (2006.01)
*A61P 11/00* (2006.01)
*A61K 9/00* (2006.01)
*C12N 15/113* (2010.01)

(52) U.S. Cl.
CPC .............. *A61K 31/40* (2013.01); *A61K 9/007* (2013.01); *A61P 11/00* (2018.01); *C12N 15/1137* (2013.01); *C12N 2310/11* (2013.01)

(58) Field of Classification Search
CPC ......... A61K 31/40; A61K 9/007; A61P 11/00; C12N 15/1137; C12N 2310/11
See application file for complete search history.

(56) References Cited

U.S. PATENT DOCUMENTS
2002/0082404 A1  6/2002 Abrahmsen et al.

OTHER PUBLICATIONS

Cholon et al (Journal of Cystic Fibrosis 17 (2018) S52-S60) (Year: 2018).*
Haggie et al (J. Biol. Chem. 292(3): 771-785, Jan. 2017) (Year: 2017).*
Pedemonte et al (Am J Physiol Cell Physiol 298: C866-C874, 2010) (Year: 2010).*
Cavosonstat (N1115) for cystic fibrosis (Cystic Fibrosis News Today, retrieved from https://cysticfibrosisnewstoday.com/cavosonstat-n91115-cystic-fibrosis/) (Year: 2017).*
Fernandes ("Ataluren Fails to Pass Muster as Treatment for Severe Form of Cystic Fibrosis", retrieved from cysticfibrosisnewstoday.com/2017/03/06/ataluren-fizzles-in-clinical-trial-against-severe-form-of-cystic-fibrosis/) (Year: 2017).*
Kelsen (AnnalsATS 13(Suppl 2):S138-S145, 2016) (Year: 2016).*
Blanchet, M. et al. "SKI-1/S1P inhibitor PF-429242 impairs the onset of HCV infection" *Antiviral Research*, 2015, pp. 94-104, vol. 115.
Xu, Y. et al. "Influence of the cystic fibrosis transmembrane conductance regulator on expression of lipid metabolism-related genes in dendritic cells" *Respiratory Research*, 2009, pp. 1-15, vol. 10, No. 26.
Written Opinion in International Application No. PCT/EP2018/060145, dated Jul. 2, 2018, pp. 1-4.

(Continued)

*Primary Examiner* — Richard A Schnizer
(74) *Attorney, Agent, or Firm* — Saliwanchik, Lloyd & Eisenschenk

(57) ABSTRACT

Activating transcription factor 6 (ATF6) is involved in cystic fibrosis transmembrane conductance regulator (CFTR) repression and understanding this inhibitory mechanism is of great interest to develop a therapeutic approach based on UPR regulation. Using site-1 protease (S1P) inhibitor (e.g. PF-429242) the inventors showed that both membrane localization and function of F508del-CFTR are partially restored. Accordingly, the present invention relates to a method of treating a disease associated with reduced CFTR function in a subject in need thereof comprising administering to the subject a therapeutically effective amount of a S1P inhibitor.

17 Claims, 3 Drawing Sheets

(56) References Cited

OTHER PUBLICATIONS

Figure 1:
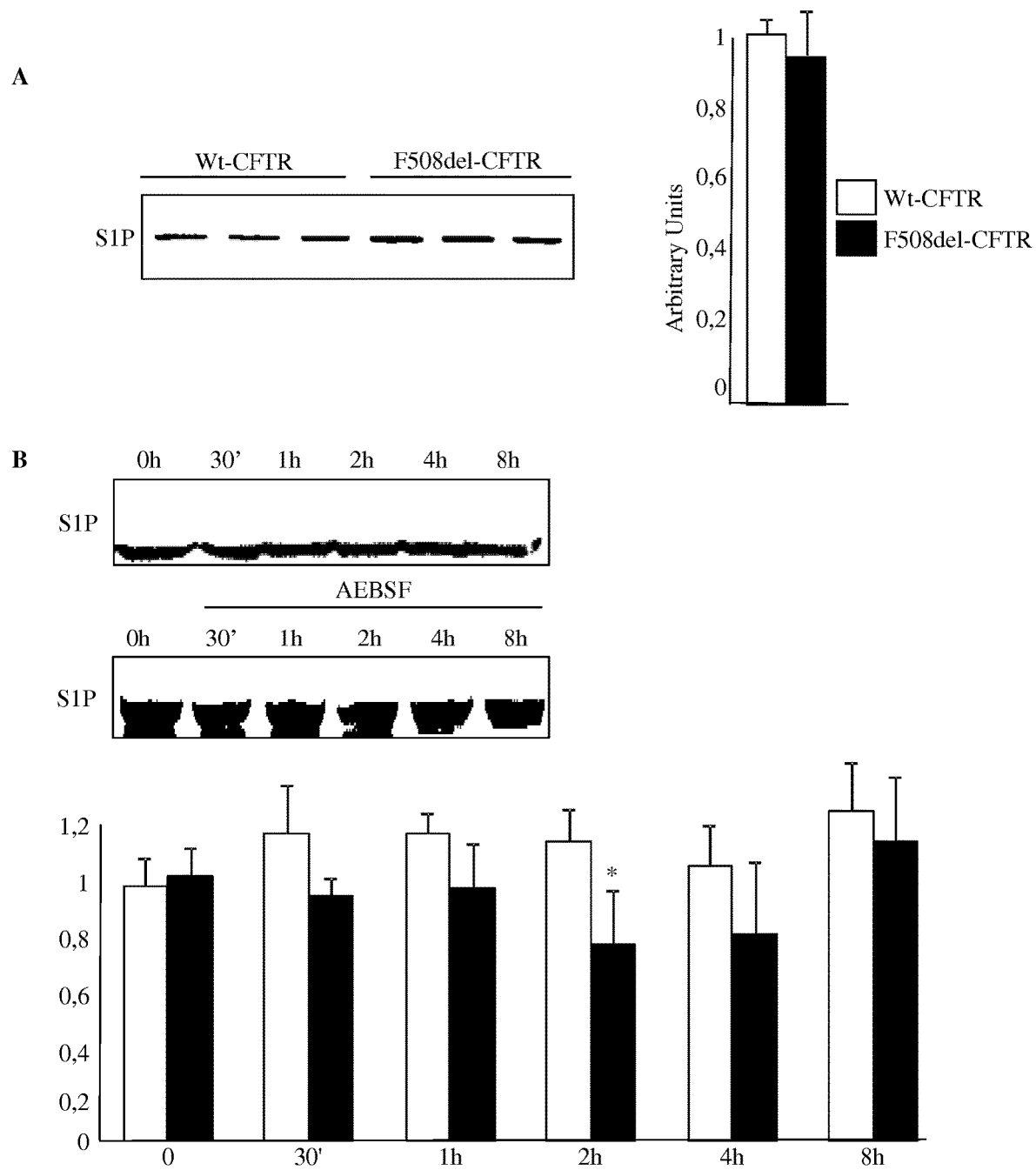

Brodzicki, J. et al. "Frequency, consequences and pharmacological treatment of gastroesophageal reflux in children with cystic fibrosis" *Med Sci Monit*, 2002, pp. CR529-537, vol. 8, No. 7.

Cell Model Resources, Cystic Fibrosis Foundation, retrieved from internet: https://cff.org/cell-model-resources#primary-cells on Nov. 19, 2021, pp. 1-10.

Cil, O. et al. "CFTR Activator Increases Intestinal Fluid Secretion and Normalizes Stool Output in a Mouse Model of Constipation" *Cellular and Molecular Gastroenterology and Hepatology*, May 2016, vol. 2, No. 3, pp. 317-327.

Cil, O. et al. "Phenylquinoxalinone CFTR activator as potential prosecretory therapy for constipation" *Translational Research*, Apr. 2017, pp. 14-26 and pp. 26.e1-26.e4, vol. 182.

Clunes, L. A. et al. "Cigarette smoke exposure induces CFTR internalization and insolubility, leading to airway surface liquid dehydration" *The FASEB Journal*, Feb. 2012, pp. 533-545, vol. 26.

Dransfield, M. T. et al. "Acquired Cystic Fibrosis Transmembrane Conductance Regulator Dysfunction in the Lower Airways in COPD" *Chest*, Aug. 2013, pp. 498-506, vol. 144, No. 2.

El-Chammas, K. I. et al. "Rectal Prolapse and Cystic Fibrosis" *JPGN*, Jan. 2015, pp. 110-112, vol. 60, No. 1.

Fogel, D. B. "Factors associated with clinical trials that fail and opportunities for improving the likelihood of success: A review" *Contemporary Clinical Trials Communications*, 2018, pp. 156-164, No. 11.

Freudenberg, F. et al. "Pathophysiological preconditions promoting mixed "black" pigment plus cholesterol gallstones in a ΔF508 mouse model of cystic fibrosis" *Am J. Physiol Gastrointest Liver Physiol*, 2010, pp. G205-G214, vol. 299.

Illing, E. et al. "Chlorogenic Acid Activates CFTR-Mediated Cl⁻ Secretion in Mice and Humans: Therapeutic Implications for Chronic Rhinosinusitis" *Otolaryngol Head Neck Surg.*, Aug. 2015, pp. 1-16, vol. 153, No. 2.

Johannesson, B. et al. "CFTR Regulates Early Pathogenesis of Chronic Obstructive Lung Disease in βENaC-Overexpressing Mice" *PloS One*, Aug. 24, 2012, pp. 1-11, vol. 78, No. 8, e44059.

Lamert, J. A. et al. "Cystic Fibrosis Transmembrane Conductance Regulator Activation by Roflumilast Contributes to Therapeutic Benefit in Chronic Bronchitis" *American Journal of Respiratory Cell and Molecular Biology*, Mar. 2014 (published in press on Oct. 9, 2013), pp. 549-558, vol. 150, No. 3.

Solomon, G. M. et al. "Therapeutic Approaches to Acquired Cystic Fibrosis Transmembrane Conductance Regulator Dysfunction in Chronic Bronchitis" *Ann Am Thorac Soc*, Apr. 2016, pp. S169-S176, vol. 13, Supplement 2.

Tzetis, M. et al. "CFTR gene mutations—including three novel nucleotide substitutions—and haplotype background in patients with asthma, disseminated bronchiectasis and chronic obstructive pulmonary disease" *Hum Genet*, Feb. 28, 2001, pp. 216-221, vol. 108.

Uc, A. et al. "Pancreatic and biliary secretion are both altered in cystic fibrosis pigs" *Am. J. Physiol Gastrointest Liver Physiol*, 2012, pp. G961-G968, vol. 303.

Wang, W. et al. "Epithelial Sodium and Chloride Channels and Asthma" *Chinese Medical Journal*, Aug. 20, 2015, pp. 2242-2249, vol. 128, Issue 16.

Zeybel, G. L. et al. "Ivacaftor and symptoms of extra-oesophageal reflux in patients with cystic fibrosis and G551D mutation" *Journal of Cystic Fibrosis*, 2017 (available online Jul. 27, 2016), vol. 16, pp. 124-131.

Hassan, T. et al. "miR-199a-5p silencing regulates the unfolded protein response in chronic obstructive pulmonary disease an α1-antitrypsin deficiency" *American Journal of Respiratory and Critical Care Medicine*, 2014, pp. 263-273, vol. 189, No. 3.

Hengstermann, A. et al. "Endoplasmic reticulum stress induced by aqueous extracts of cigarette smoke in 3T3 cells activates the unfolded-protein-response-dependent PERK pathway of cell survival" *Free Radical Biology & Medicine*, 2008, pp. 1097-1107, vol. 44, No. 6.

Jorgensen, E. et al. "Cigarette smoke induces endoplasmic reticulum stress and the unfolded protein response in normal and malignant human lung cells" *BMC Cancer*, 2008, pp. 1-30, vol. 8, No. 229.

Kelsen, S. G. et al. "Cigarette Smoke Induces an Unfolded Protein Response in the Human Lung, A Proteomic Approach" *Am J Respir Cell Mol Biol*, 2008, pp. 541-550, vol. 38, No. 5.

Merali, S. et al. "Analysis of the Plasma Proteome in COPD: Novel Low Abundance Proteins Reflect the Severity of Lung Remodeling" *COPD*, Apr. 2014, pp. 1-19, vol. 11, No. 2.

Min, T. et al. "Critical role of proteostasis-imbalance in pathogenesis of COPD and severe emphysema" *J Mol Med (Berl)*, Jun. 2011, pp. 1-30, vol. 89, No. 6.

Naiel, S. et al. "Protein Misfolding and Endoplasmic Reticulum Stress in Chronic Lung Disease, Will Cell-Specific Targeting Be the Key to the Cure?" *Chest*, May 2020, pp. 1207-1220, vol. 157, No. 5.

Ribeiro, C. M. P. et al. "Endoplasmic Reticulum Stress in Chronic Obstructive Lung Diseases" *Current Molecular Medicine*, 2012, pp. 1-12 (including cover page), vol. 12, No. 7.

Wei, J. et al. "Protein Misfolding and Endoplasmic Reticulum Stress in Chronic Lung Disease" *Chest*, Apr. 2013, pp. 1098-1105, vol. 143, No. 4.

Wixted, W. E. et al. "A model to identify novel targets involved in oxidative stress-induced apoptosis in human lung epithelial cells by RNA interference" *Toxicology in Vitro*, 2010 (available online Aug. 23, 2009), pp. 310-318, vol. 24.

\* cited by examiner

A

B

METHODS AND PHARMACEUTICAL COMPOSITIONS FOR THE TREATMENT OF DISEASES ASSOCIATED WITH REDUCED CFTR FUNCTION

CROSS-REFERENCE TO RELATED APPLICATION

This application is the U.S. national stage application of International Patent Application No. PCT/EP2018/060145, filed Apr. 20, 2018.

FIELD OF THE INVENTION

The present invention relates to methods and pharmaceutical compositions for the treatment of diseases associated with reduced CFTR function.

BACKGROUND OF THE INVENTION

Cystic fibrosis transmembrane conductance regulator (CFTR) is expressed in a variety of cells types, including absorptive and secretory epithelia cells, where it regulates anion flux across the membrane, as well as the activity of other ion channels and proteins. CFTR is a member of the ATP-binding cassette transporters and functions as a chloride (Cl—) channel. In epithelial cells, normal functioning of CFTR is critical for the maintenance of electrolyte transport throughout the body, including respiratory and digestive tissue. Mutations in CFTR typically results in cystic fibrosis ("CF"), the most common fatal genetic disease in humans. The most common mutation in CF is a missing phenylalanine at position 508 (F508del-CFTR), which occurs in the first nucleotide-binding domain (NBD1) of the CFTR protein. The pathology associated with F508del-CFTR is believed to be a failure of the mutated protein to traffic correctly to the plasma membrane which leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency. In addition, the majority of males with cystic fibrosis are infertile and fertility is decreased among females with cystic fibrosis. Interestingly, some studies indicate that the F508del-CFTR protein can function as a cAMP-dependent Cl— channel, suggesting that if conditions could be created to allow the F508del-CFTR protein to exit the ER and reach the membrane, it might partially correct the CF defect. The cellular phenomenon of defective ER processing of CFTR by the ER machinery, has been shown to be the underlying basis not only for CF disease, but for a wide range of other diseases. Examples of such diseases include, but are not limited to, chronic obstructive pulmonary disease (COPD), asthma, smoke induced COPD, chronic bronchitis, rhinosinusitis, constipation, gastro-esophageal reflux disease, gallstones, rectal prolapse, and inflammatory bowel disease. Accordingly, there is a need for potent and selective CFTR potentiators of wild-type and mutant forms of human CFTR. Recently, the inventors showed by using siRNA, that decreased ATF6 expression induces increased cAMP-dependent halide flux through F508del-CFTR due to its increased membrane localization (Biochim Biophys Acta. 2007 December; 1772(11-12): 1236-49).

SUMMARY OF THE INVENTION

The present invention relates to methods and pharmaceutical compositions for the treatment of diseases associated with reduced CFTR function. In particular, the present invention is defined by the claims.

DETAILED DESCRIPTION OF THE INVENTION

The first object of the present invention relates to a method of treating a disease associated with reduced CFTR function in a subject in need thereof comprising administering to the subject a therapeutically effective amount of a site 1 protease (S1P) inhibitor.

As used herein, the term "CFTR" has its general meaning in the art and refers to cystic fibrosis transmembrane conductance regulator. The term "reduced CFTR function" as used herein means less than normal CFTR or less than normal CFTR function. According to the present invention the reduced CFTR function results from a defective endoplasmic reticulum (ER) processing of CFTR by the ER machinery which leads to a mislocalization of the protein.

In some embodiments, the subject suffers from a disease associated with reduced CFTR function due to mutations in the gene encoding CFTR or environmental factors (e.g., smoke). A mutation thereof capable of regulator activity, including, but not limited to, F508del-CFTR, R117H CFTR, and G551D CFTR (see, e.g., Worldwide Website genet.sickkids.on.ca/cftr, for CFTR mutations). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In some embodiments, the subject suffers from a disease selected from the group consisting of chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gastro-esophageal reflux disease, gastrointestinal malignancies, inflammatory bowel disease, constipation, diabetes, arthritis, osteoporosis, and osteopenia.

As used herein, the term "treatment" or "treat" refer to a curative or disease modifying treatment, including treatment of patient suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "S1P" has its general meaning in the art and refers to site-1 protease. The term is also known as subtilisin/kexin-isozyme 1 (SKI-1), and is an enzyme (EC 3.4.21.112) that in humans is encoded by the MBTPS1 gene (Gene ID: 8720). Exemplary human nucleic and amino acid sequences are represented by the NCBI reference sequences NM_003791.3 and NP_003782 respectively.

As used herein, the term "S1P" inhibitor refers to any compound capable of inhibiting the activity or expression of S1P. In particular, the S1P inhibitor of the present invention is capable of restoring the function of CFTR "by correcting the defective endoplasmic reticulum (ER) processing of CFTR. In particular, the S1P inhibitor of the present invention will restore the localization of CFTR at the membrane. The restoration of CFTR function may be determined by any assay well known in the art and typically the assay as described in the EXAMPLE section of the present specification.

In some embodiments, the S1P inhibitor is small organic molecule as PF-429242 (4-(diethylaminomethyl)-N-[2-(2-methoxyphenyl)ethyl]-N-pyrrolidin-3-ylbenzamide; dihydrochloride).

In some embodiments, the S1P inhibitor is an inhibitor of S1P expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of S1P mRNA by binding thereto and thus preventing protein translation or increasing mRNA degradation, thus decreasing the level of S1P, and thus activity, in a cell. For example, antisense oligonucleotides of at least about 15 bases and complementary to unique regions of the mRNA transcript sequence encoding S1P can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. S1P gene expression can be reduced by contacting a patient or cell with a small double stranded RNA (dsRNA), or a vector or construct causing the production of a small double stranded RNA, such that S1P gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing S1P. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR). In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from *Streptococcus pyogenes*. The CRISPR/Cas9 system has been described in U.S. Pat. No. 8,697,359 B1 and US 2014/0068797. In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

By a "therapeutically effective amount" of the S1P inhibitor of the invention as above described is meant a sufficient amount of the compound. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the S1P inhibitor is administered to the subject using any suitable method that enables the S1P inhibitor to reach the lungs. The S1P inhibitor may be administered to a subject by any suitable means known in the art. In some embodiments, the S1P inhibitor is administered to the subject systemically (i.e. via systemic administration). Thus, in some embodiments, the S1P inhibitor (as described above) is administered to the subject such that it enters the circulatory system and is distributed throughout the body. In some embodiments, the S1P inhibitor is administered to the subject by local administration, for example by local administration to the lungs. In some embodiments, the S1P inhibitor is delivered by any device adapted to introduce one or more therapeutic compositions into the upper and/or lower respiratory tract. The devices may be adapted to deliver the therapeutic compositions of the invention in the form of a finely dispersed mist of liquid, foam or powder. The device may use a piezoelectric effect or ultrasonic vibration to dislodge powder attached on a surface such as a tape in order to generate mist suitable for inhalation. The devices may use any propellant system known to those in the art including, but not limited to, pumps, liquefied-gas, compressed gas and the like. Devices of the present invention typically comprise a container with one or more valves through which the flow of the therapeutic composition travels and an actuator for controlling the flow. The devices suitable for administering the constructs of the invention include inhalers and nebulisers. Various designs of inhalers are available commercially and may be employed to deliver the medicaments of the invention. These include the Accuhaler, Aerohaler, Aerolizer, Airmax, Autohaler, Clickhaler, Diskhaler, Easi-breathe inhaler, Fisonair, Integra, Jet inhaler, Miat-haler, Novolizer inhaler, Pulvinal inhaler, Rotahaler, Spacehaler, Spinhaler, Syncroner inhaler and Turbohaler devices. Thus, in some embodiments, the delivery is done by means of a nebulizer or other aerosolisation device provided the integrity of the S1P inhibitor is maintained.

The S1P inhibitor of the invention may be combined with pharmaceutically acceptable excipients, and optionally sustained-release matrices, such as biodegradable polymers, to form therapeutic compositions. “Pharmaceutically” or “pharmaceutically acceptable” refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Galenic adaptations may be done for specific delivery in the small intestine or colon. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising S1P inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The S1P inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifusoluble agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. The S1P inhibitor of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the S1P inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1. Expression of S1P in cells expressing Wt- and F508del-CFTR cells, with and without AEBSF treatment. A. The left image shows a representative immunodetection experiment of the S1P protein (110 kDa) in cells expressing either Wt- or F508del-CFTR. The right image shows the corresponding statistical analysis of S1P expression (n=6). No significant difference was observed between the two cell lines. B. The upper image is a representative gel showing S1P expression in untreated cells (n=3). The middle image is a representative gel showing S1P expression in AEBSF treated cells (300 µM) at different time points (0.5; 1; 2; 4 or 8 hours; n=4 to 5). The bottom image is the statistical analysis of S1P expression in untreated CFBE41o−/F508del cells and in treated cells. Whereas S1P expression tended to be decreased in treated cells after 0.5 hour treatment, significance was only observed at the 2 hours time point.

Figure 2:
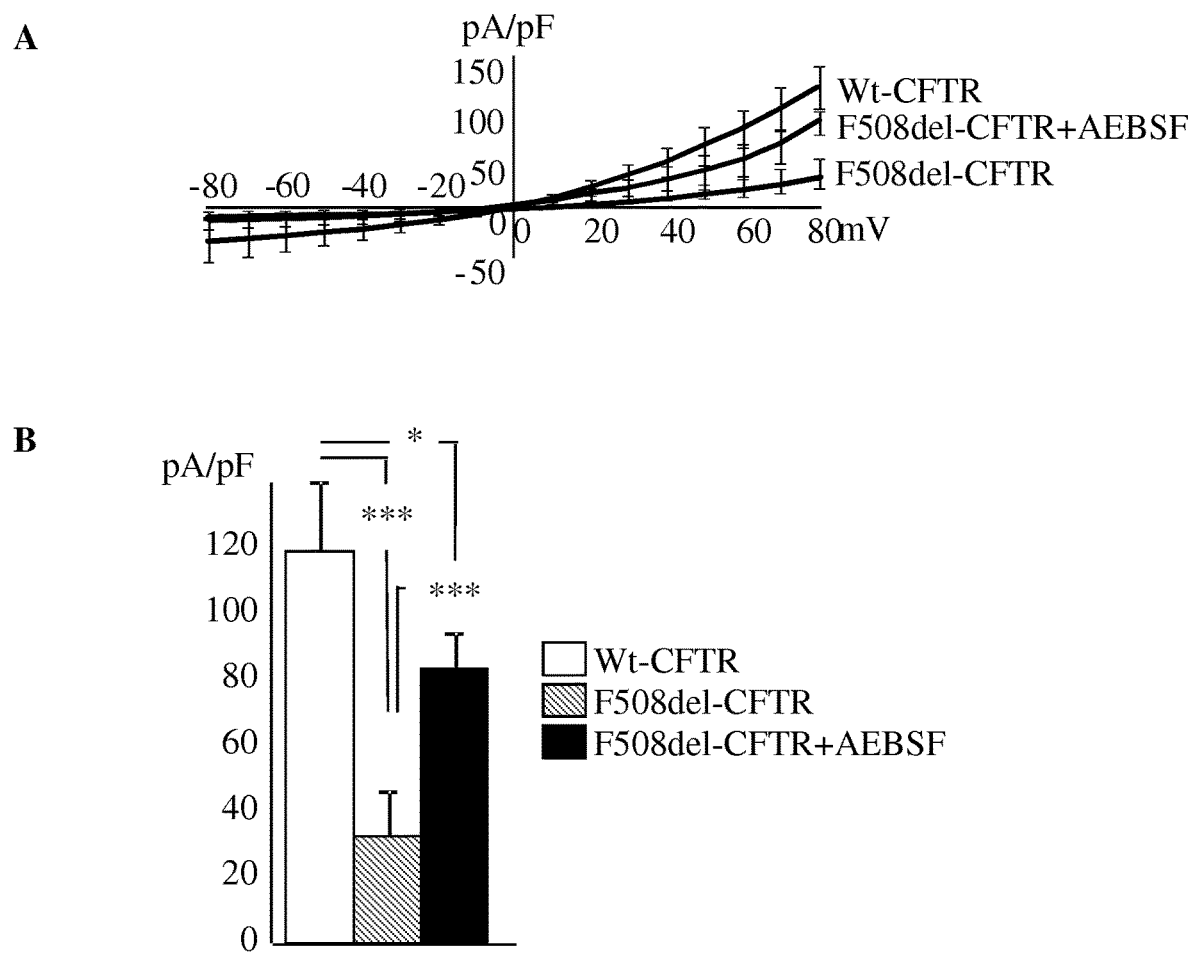

FIG. 2. F508del-CFTR Cl— channel activity is partially restored by AEBSF in cells expressing F508del-CFTR. A. The top image shows a representative current-voltage (I-V) relationships for CFTR channels in Wt-CFTR (light grey), F508del-CFTR (dark grey) and in AEBSF treated F508del-CFTR cells (300 µM, 8 hours). B. The bar graphs show the statistical analysis of CFTR function in Wt-CFTR cells (n=5), in F508del-CFTR cells (n=6) and in treated F508del-CFTR cells (300 µM AEBSF, 8 hours, n=4). The analysis was performed using pA/pF values at +80 mV. As expected, Cl— currents were significantly lower in cells expressing F508del-CFTR than in cells expressing Wt-CFTR. Despite Cl— currents were significantly lower in treated F508del-CFTR cells than in cells expressing Wt-CFTR, an important and significant increase (+153%) was observed in treated F508del-CFTR cells when compared to untreated cells expressing F508del-CFTR.

Figure 3:
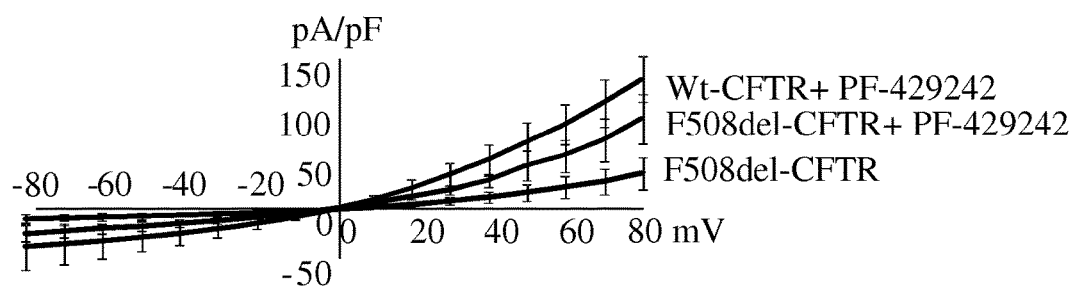
Figure 3:
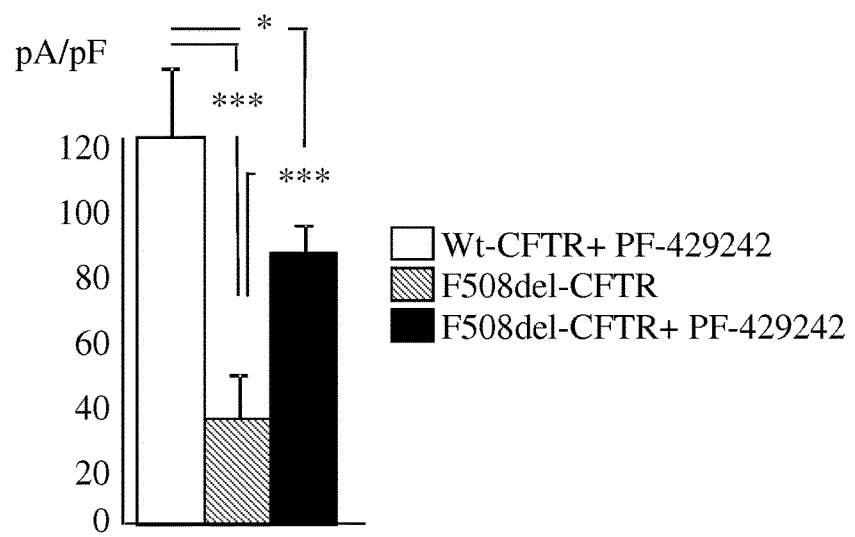

FIG. 3. F508del-CFTR Cl⁻ channel activity is partially restored by PF-429242 in cells expressing F508del-CFTR. A. The top image shows a representative current-voltage (I-V) relationships for CFTR channels in Wt-CFTR (light grey), F508del-CFTR (dark grey) and in PF-429242 treated F508del-CFTR cells (10 µM, 8 hours). B. The bar graphs show the statistical analysis of CFTR function in Wt-CFTR cells (n=5), in F508del-CFTR cells (n=6) and in treated F508del-CFTR cells (10 µM PF-429242, 8 hours, n=5). The analysis was performed using pA/pF values at +80 mV. As expected, Cl⁻ currents were significantly lower in cells expressing F508del-CFTR than in cells expressing Wt-CFTR. Despite Cl⁻ currents were significantly lower in treated F508del-CFTR cells than in cells expressing Wt-CFTR, an important and significant increase (+152%) was observed in treated F508del-CFTR cells when compared to untreated cells expressing F508del-CFTR. These results were fully comparable to those obtained with AEBSF, as shown in FIG. 2.

EXAMPLE

Material & Methods:
Cell Culture and Regents

The CFBE41o–cells purchased from Professor D. C. Gruenert (San Francisco, Calif., U.S.A.) were human bronchial epithelial cells endogenously expressing the F508del-CFTR obtained from a CF patient homozygous for the F508del mutation [51;52]. The cells used in experiments were the transduced CFBE41o−/WT also called CFBE41o−/corrected (CFBE41o−/corr) and CFBE41o−/F508del cells, and were cultured as previously described [53]. These cells will be also called cells expressing Wt-CFTR and cells expressing F508del-CFTR in the manuscript. Cell culture media and supplements were purchased from Lonza (Basel, Switzerland) and CliniSciences (Nanterre, France). To inhibit ATF6 activation, cells were incubated with 300 µM of the serine protease inhibitor 4-(2-Aminoethyl) benzenesulfonyl fluoride hydrochloride (AEBSF) purchased from Servilab. In some experiments, ATF6 activation was blocked by the use of 10 µM PF-429242 (4-[(Diethylamino)methyl]-N-[2-(2-methoxyphenyl)ethyl]-N-(3R)-3-pyrrolidinylbenzamide, from Tocris).

Immunoblotting

Untreated or AEBSF treated cells were rinsed twice with cold PBS. For total cell lysate preparation, cells were lysed in RIPA buffer (25 mM Tris-HCl pH 7.5, 150 mM NaCl, 1% Triton X-100, 1% Na-Deoxycholate, 0.1% SDS, 10 mM iodoacetamide, 100 µM PMSF) supplemented with fresh protease-inhibitor cocktail (Complete tablets—EDTA free, Roche, Basel, Switzerland) added extemporaneously at a final concentration of 40 µl/ml (30 min on ice). Lysates were centrifugated (15 min, 16000 g, 4° C.). For nuclear preparation, cells were washed twice with cold PBS, and lysed with buffer A (10 mM HEPES pH 7.9, 1.5 mM $MgCl_2$, 10 mM KCl, 2 mM EDTA, 0.5 mM DTT, 0.20% NP40 and protease-inhibitor cocktail) during 15 min at 4° C. Lysates were then centrifuged (1,500×g, 2 min, 4° C.) and the supernatants (cytosolic fraction) were removed in a new tube. The pellet was washed twice in buffer B (Buffer A without NP40) and lysed with buffer C (20 mM HEPES pH 7.9, 1.5 mM $MgCl_2$, 450 mM KCl, 2 mM EDTA, 2 mM EGTA, 0.5 mM DTT, 25% Glycerol and protease-inhibitor cocktail) during 1 h vortexing 2200 rpm. Lysates were then centrifuged (14,000×g, 10 min, 4° C.) and supernatant (nuclear fraction) was removed in a new tube. Protein concentrations were determined using Lowry's methodology with the bovine serum albumin used as a standard [54].

For each sample equal amount of total or nuclear proteins was loaded on a polyacrylamide gel and resolved by SDS-PAGE (10%). Samples were then transferred onto a PVDF membrane (EMD Millipore, Billerica, Mass., United States). After blotting, membranes were blocked with 5% (w/v) non-fat dried skimmed milk in PBS-0.1% Tween20 (PBST). Blots were then probed overnight at 4° C. with the primary antibodies listed hereafter: Rabbit polyclonal anti-ATF6 antibody (#09-069, EMD Millipore), Rabbit polyclonal anti-S1P antibody (H-300) (#SC-20757, SantaCruz Biotechnology), Rabbit polyclonal anti-GRP78 antibody (H-129) (#SC-13968, SantaCruz Biotechnology). Membranes were further incubated 1 h at room temperature with the appropriate horseradish peroxidase (HRP) conjugated secondary antibody diluted in PBST (1/20,000): Goat anti-rabbit (#A0545, Servilab). Blots were developed by enhanced chemiluminescence kit (ECL Plus, GE Healthcare) and analyzed using Chemi-Smart 5100 ECL imaging system (Vilber Lourmat). The relative intensity of each band was quantified by densitometry using BIO-1D software (Vilber Lourmat). Each value was normalized by blue coomassie staining or the G3PDH signal obtained in the same lane on the same blot probed with mouse monoclonal antibody anti-G3PDH (#H86504M, Meridian Life Science®, Inc.) diluted in PBST (1/30,000).

Patch-Clamp Experiments

Whole-cell patch-clamp recordings were obtained with the patch clamp system Port-a-Patch® (Nanion Technologies GmbH, Germany) as previously described [74;75]. Untreated or AEBSF treated cells were incubated with the external solution (140 mM NaCl, 2 mM $CaCl_2$, 1 mM $MgCl_2$, 10 mM Hepes, 5 mM D-glucose monohydrate, pH 7.4, 298 mOsmol) before recording. The internal solution used was 50 mM CsCl, 10 mM NaCl, 60 mM Cs-Fluoride, 20 mM EGTA, 10 mM Hepes/CsOH, and 5 mM Mg-ATP (Mg salt); pH 7.2; 285 mOsmol. CFTR activation and CFTR inhibition was done using the CFTR-activator (10 mM forskolin and 30 mM genistein both from Sigma) and the CFTR-inhibitor (10 mM CFTRinh172, Sigma) solution respectively, that were added to the external solution. Voltage steps (100 ms) from a holding potential of −80 mV, from −80 mV to +80 mV (10 mV increments) were applied. Data were captured using the Patchmaster program (Nanion Technologies GmbH, Germany) and currents normalized by membrane capacitances to remove variability due to differences in the cell sizes. Results were presented as graphic representations of I/V relationship and as bar graphs after statistical analysis of the normalized values, at +80 mV.

Cell Surface Detection of CFTR

BHK cells stably expressing WT-CFTR or F508del-CFTR were graciously given by Dr. John W. Hanrahan (McGill University). A 3-Haemaglutinin (HA)-epitope tag was inserted in the fourth extracellular loop of CFTR in these cell lines [76]. Cells were cultured in Dulbecco's modified Eagle medium (Lonza, Switzerland) supplemented with 10% fetal bovine serum. Cells were washed three times with cold 1×PBS (Eurobio, France) plus bovine serum albumine (BSA, 0.5%) and incubated 1 h at 4° C. with an anti-HA antibody (BioLegend, USA) diluted (1/250) in 1×PBS plus 0.5% BSA. Cells were washed three times with cold 1×PBS, scraped and centrifugated (300×g, 3 min, 4° C.). Cells pellets were suspended in RIPA buffer for 30 min on ice, centrifuged (16000×g, 15 min, 4° C.) and total protein concentration of supernatant was determined using Lowry's method, using BSA as a standard. Protein G magnetic beads (Thermo Fisher Scientific, USA) were equilibrated with cold RIPA buffer. Lysates were then incubated with the magnetic beads (100 µl of magnetic beads per mg of total protein) at 4° C. during for 2 h. Beads were then rinsed three times in cold RIPA buffer and proteins were eluted with 2× sample buffer containing 2-mercaptoethanol (20 min, 37° C.). Finally, eluates were subjected to SDS/PAGE (7.5%) and transferred onto a PVDF membrane. Membrane was blocked with 5% (w/v) dried skimmed milk in PBS (0.1%) with Tween20, probed overnight at 4° C. with the anti-HA antibody (1/500) in 5% non-fat dried milk in PBST. Membranes were further washed and incubated 1 h at RT with HRP conjugated anti-mouse antibody (1/20000; Santa Cruz Biotechnology, USA). Blots were developed by enhanced chemiluminescence kit (ECL Plus, GE Healthcare, USA) and analyzed using Chemi-Smart 5100 ECL imaging system (Vilber Lourmat, Germany).

Two-Dimensional Gel Electrophoresis (2-DE) and Mass Spectrometry

100 µg of total proteins from untreated or AEBSF treated cells were used for experiments. Each protein sample was first diluted in DeStreak Rehydration Solution (GE Healthcare, Chalfont St Giles, UK) which contains optimized concentrations of urea, thiourea, CHAPS, DeStreak Reagent and appropriate IPG buffer. Passive rehydration of Immobiline DryStrip gels (7 cm, pH 3-10 NL, GE Healthcare) with samples was performed during 8 hours. Once rehydration completed, Immobiline DryStrip gel are transferred in the Manifold on Ettan IPGphor 3 (GE Healthcare) for first dimension isoelectric focusing (IEF). IEF protocol used is divided in five steps: 1—Step 300 V, 200 Vhr; 2—Grad 1000 V, 300 Vhr; 3—Grad 5000 V, 4500 Vhr; 4—Step 5000V, 9000 Vhr; 5—Step 300V, 12-15 h. Second-dimension separation is performed immediately after IEF is completed. Immobiline DryStrip gels are equilibrated (15 min at room temperature) in two SDS equilibration buffers (6 M urea, 75 mM Tris-HCl pH=8.8, 30% Glycerol, 2% SDS, 0.0002% bromophenol blue+DTT or iodoacetamide) before SDS-PAGE. Electrophoresis was performed with lab-cast gels (1 mm, Bis-Tris 10%) in 1× Tris-Glycine-SDS buffer (BioRad, Hercules, Calif., USA) at 120 V for 2 h 30. The 2-DE gels were stained with a G-250 Coomassie blue solution, scanned and finally digitalized using the GS-800 Calibrated Densitometer (Bio-Rad). Gel alignment, spot detection and quantification were done using the PDQuest software (PDQuest Basic-8.0.1, BioRad). Data are the means of 4 gels from 4 different experiments.

MS analysis of the differentially expressed proteins was performed at the «Plateforme d'Analyse Protéomique de Paris Sud Ouest, France» facility, using LC-MS/MS. Enzymatic digestion was realised by 50 ng Trypsin (enzyme/protein ratio: 1/50, 37° C., overnight). Supernatant was used for extraction. LC-MS/MS analysis was done using a LTQ-Orbitrap Spectrometer. Nano HPLC (Dionex RSLC UltiMate3000) was used, followed by MS (Scan range: 400-1500 m/z, fragmentation: CID, Energy of collision: 35%, Cycle for fragmentation (TopN): Top8). Data were converted to mzXML using MS convert (ProteoWizard v 3.0.8934). Databases interrogation was performed by X!Tandem Piledriver (v2015.04.01.1) and X!Tandem Pipeline (v 3.4.2<<Elastine Durcie>>).

Protein-Protein Interactions (PPI) Analysis

PPI networks were searched using STRING 10.0 (Search Tool for the Retrieval of Interacting Genes and Proteins, string-db.org/). The protein's names were used as an initial input. The search parameters were as following: all PPI prediction methods were enabled, except for High-throughput Lab Experiments; maximum of 5 interactions by node; cut-off criterion of combined score ≥0.9 (highest confidence permitted in STRING); *Homo sapiens*.

Statistics

Results are expressed as mean±standard error of the mean (SEM). Differences between experimental groups were evaluated by a two-tailed unpaired Student's t test and were considered statistically significant when $p<0.05$ (*); $p<0.01$ () and $p<0.001$ (*).

Results:

F508del-CFTR Triggers UPR in CFBE41o–/F508del Cells

Because BiP is the main sensor and regulator of the UPR [25-28], we used it as a reporter of UPR triggering. The expression of BiP in total cell lysates of CFBE41o–/WT and CFBE41o–/F508del cells was measured by western blot. The comparison of BiP expression between these cells expressing either Wt-CFTR or F508del-CFTR, showed that BiP was significantly overexpressed in CFBE41o–/F508del cells. Thus our results show that the UPR is activated in cells expressing F508del-CFTR, in accordance with our previous results [42]. We also assessed full length ATF6 (90 kDa) expression in total cell lysates of CFBE41o–/WT or CFBE41o–/F508del cells by western blot. We measured its expression level in both cell types and found that full length ATF6 expression was significantly higher in cells expressing F508del-CFTR than in Wt-CFTR cells. During UPR process, ATF6 is cleaved and its active form (50 kDa) is released and translocated to the nucleus. Therefore, the cleaved form of ATF6 and its translocation to the nucleus were analyzed. Cytoplasmic and nuclear fractions of Wt-CFTR and F508del-CFTR cells were prepared and ATF6 expression was measured in the nuclear fractions by western blot. We found that the expression of the cleaved form of ATF6 was significantly increased in the nucleus of cells expressing F508del-CFTR, which is another evidence of the UPR activation in F508del-CFTR cells.

Therefore, as previously described [42, 43, 46], we found that UPR is triggered in cells expressing the F508del-CFTR protein.

ATF6 Inhibition Represses UPR in CFBE41o–/F508del Cells

UPR triggering in cells expressing F508del-CFTR being shown, we assessed the effect of an AEBSF treatment upon UPR and ATF6. First of all, we defined the best conditions to use this serine protease inhibitor AEBSF for our experiments and performed a 1 hour pre-treatment of the cells with 300 µM AEBSF to evaluate its effects on the UPR and ATF6. As described above, we analyzed UPR by measuring the expression of BiP and evaluated both expression and activation of ATF6.

We measured BiP expression by western blot in total cell lysates of untreated or AEBSF treated cells expressing F508del-CFTR. Untreated cells showed no significant variation of BiP expression over time. In the presence of AEBSF, a significant decrease of BiP expression was observed after 4 hours of treatment. The comparison of BiP expression between untreated and AEBSF treated cells, for each time point, was performed. Significant decreases at the 4 and 8 hours time points in the presence of AEBSF were observed. Therefore, these results demonstrated an inhibitory effect of AEBSF upon BiP expression in UPR activated F508del-CFTR cells. AEBSF is thus a repressor of the UPR in these cells. The expression of full length ATF6 was evaluated by western blot in total cell lysates of untreated or AEBSF treated cells expressing F508del-CFTR. No significant difference of ATF6 expression over time in untreated cells was observed. In AEBSF treated cells expressing F508del-CFTR, a significant increased expression was observed after 4 and 8 hours of treatment, when compared to the zero time point. Moreover, the comparison between untreated and AEBSF treated cells for each time point was done and showed significant decreases after 0.5, 1 and to 2 hours and a significant increase after 8 hours in AEBSF pre-treated cells. We further estimated ATF6 activation by assessing its presence in nuclear fractions of untreated and AEBSF treated cells expressing F508del-CFTR. In untreated cells we detected the cleaved form of ATF6 in the nuclear fractions. These experiments showed no significant variation of ATF6 expression over time. We further studied ATF6 activation in AEBSF treated cells and we observed significant decreases at the 2 and 4 hours treatment, when compared to the zero time point. Finally, we performed the comparison between untreated and AEBSF treated cells for each time point and observed significant decreased expression of the 50 kDa form of ATF6, from 1 to 8 hours, in the nuclear fraction of AEBSF treated cells. Thus, our results showed that AEBSF inhibits ATF6 activation in cells expressing F508del-CFTR. Since ATF6 activation is due to a cleavage by S1P, we analyzed S1P expression in cells expressing Wt-CFTR and in cells expressing F508del-CFTR (FIG. 1A). We measured basal expression of S1P in total cell lysates from both cells types by western blot (FIG. 1A, left panel). No significant difference in S1P expression in cells expressing either Wt-CFTR or F508del-CFTR was observed (FIG. 1A, right panel). S1P expression was measured by western blot in total cell lysates of untreated and AEBSF treated cells expressing F508del-CFTR (FIG. 1B). Experiments performed with untreated cells showed no significant difference during time (FIG. 1B, upper panel). The cells expressing F508del-CFTR were then submitted to the AEBSF treatment. As shown in FIG. 1B, no significant variation was observed over time except for the 2 hours time point (FIG. 1B, bar graphs). Finally, the comparison of S1P expression between untreated and AEBSF treated cells for each time point showed no significant difference (FIG. 1B).

ATF6 Inhibition by AEBSF Partially Restores the Cl⁻ Channel Function of F508del-CFTR To appreciate the effect of ATF6 inhibition by AEBSF on CFTR Cl— channel function we performed patch-clamp experiments, in the whole cell configuration, on untreated or AEBSF treated cells expressing F508del-CFTR (FIG. 2). The used experimental conditions were previously described [75, 77]. CFTR activators and inhibitor [75, 77] were used for patch-clamp experiments and were efficient to stimulate or inhibit the CFTR Cl— channel activity, respectively, showing the specificity of the recorded signals (data not shown). We first compared the CFTR's function between cells expressing Wt-CFTR and cells expressing F508del-CFTR. Corresponding I/V curves are shown in FIG. 2A. Four to six independent experiments were realized from different cell cultures and the statistical analysis showed that the mean cell Cl— currents in CFBE41o−/WT cells (118.8±21.09 pA/pF) were significantly higher than those recorded in CFBE41o−/F508del cells (32.98±14.71 pA/pF) (FIG. 2B). Unsurprisingly, our results confirmed the altered Cl— channel activity of the F508del mutated CFTR in CFBE/F508del cells. Then we analysed the impact of an 8 hours AEBSF treatment on F508del-CFTR Cl— channel activity (FIG. 2A). This time point was chosen because at this time point, all our UPR markers indicated that AEBSF inhibits UPR. Four independent experiments were performed with AEBSF treated cells expressing F508del-CFTR. A significant increase of the mean cell Cl— currents in AEBSF treated cells (83.42±11.51 pA/pF), compared to CF untreated cells (32.98±14.71 pA/pF) was observed (FIG. 6B). Therefore, our results showed that AEBSF induced a 2.5 fold increase of the F508del-CFTR's Cl— function, reaching the limit of significance of the Wt-CFTR Cl— function (118.8±21.09 pA/pF). Therefore, our results show the partial restoration of the F508del-CFTR Cl— function in CFBE/F508del cells treated with AEBSF and suggested that using AEBSF to inhibit the ATF6 branch of the UPR in CF cells could represent a potential treatment for CF patients expressing the F508del-CFTR mutated protein.

We found that AEBSF inhibits ER stress-induced proteolysis of ATF6 and restores the Cl channel function of F508del-CFTR. Because of the importance of these results, we assessed the effect of another S1P inhibitor. Indeed, the observed recovery of the function of F508del-CFTR could be due to AEBSF itself. We used a specific S1P inhibitor, the amino-pyrrolidine amide compound PF-429242, which efficiently blocks the S1P-mediated cleavage of ATF6 upon ER stress [78]. The effect of PF-429242 upon F508del-CFTR function was assessed using the same methodology as for AEBSF. I/V curves were drawn (FIG. 3A). It was observed that the currents through F508del-CFTR were higher in PF-429242 treated cells (n=6) than in untreated cells (n=5). The statistical analysis (FIG. 3B) showed that PF-429242 treatment leads to a significant increased function of F508del-CFTR (82.67±22.26 pA/pF) and that this increased function is similar to the increase observed with AEBSF.

Cell Surface Expression of F508del-CFTR is Increased when ATF6 is Inhibited

To explain the partial restoration of the channel function of F508del-CFTR when ATF6 is inhibited by AEBSF, we assessed the rescue of CFTR within cell membranes. We used BHK Chinese hamster ovary cells because they are not polarized and therefore CFTR's function can be studied independently of sophisticated trafficking and regulation [79]. Despite they are less relevant regarding CFTR biogenesis, they represent a simple model. Furthermore, when transfected they express high amounts of CFTR. This permits a more direct characterization of a direct effect of a compound upon CFTR function. The used BHK cells did express CFTR with a 3-Haemaglutinin (HA)-epitope tag on the fourth extracellular loop [76]. The tag was recognized by an anti-HA antibody which was directly added to the culture medium and recovered by magnetic beads and detected by immunoblot. The mature form of CFTR (C band, 170 kDa) was observed in the cells expressing Wt-CFTR and was absent in F508del-CFTR cells. In cells expressing F508del-CFTR, the mature form of CFTR was only observed after AEBSF treatment, indicating that ATF6 inhibition induces the glycosylation of F508del-CFTR and likely its exportation to the membrane.

Differentially Expressed Proteins when ATF6 is Inhibited

In order to depict differentially expressed proteins after ATF6 inhibition, cell lysates of untreated and treated cells were submitted to 2-DE. 4 gels were performed with both cell types and spots were analyzed by PDQuest software (BioRad). 404 and 408 spots were detected in untreated and treated cell lysates, respectively. Among spots showing variations in their expression and according to the parameters used for the detection, 4 spots were increased (above 2 fold) in untreated cells and 4 spots were increased in cells with inhibited ATF6. These 8 spots were further analyzed by MS. This analysis led to the identification of 6 different proteins. HNRNPH1 and HNRH3 were found to be decreased whereas, PDIA3 (Grp58), HSP7C, GRP75 and HSP71 were found to be increased, after ATF6 inhibition.

PPI Networks of the Differentially Expressed Proteins when ATF6 is Inhibited

For a better description of the depicted proteins, we search for their potential interactions using the 10.0 version of STRING [80]. We used the basic interaction unit in STRING for functional association between proteins, derived from known experimental data. For HNRNPH1, HNRH3, PDIA3 (Grp58), HSP7C, GRP75 and HSP71 we searched for high confidence (≥0.9) interactions and retrieved independent graphs. Unexpectedly, we observed that the proteins shared Ubiquitin C (UBC) as a common interacting partner and we drew a global graph showing this interaction. We also observed that HSP7C and HSP71 directly interact with CFTR.

Discussion:

The most common genetic form of CF is due to the F508del mutation in the CFTR gene. This mutation leads to an incorrectly folded CFTR protein which is retained in the ER and partially degraded. This accumulation of unfolded F508del-CFTR protein in the ER triggers the UPR adaptive response [42, 43, 52]. To cope with unfolded proteins accumulated in the ER, cells transiently diminish their translational and transcriptional activity. In parallel they activate genes encoding ER-resident chaperones such as BiP and folding enzymes, with the aim of increasing the folding capacity of the ER. The UPR transducer ATF6 and ER stress sensor BiP are widely used as UPR markers [40, 80]. ATF6 is a type II transmembrane glycoprotein anchored in the ER which is activated by proteolysis by S1P in response to ER stress [58, 69]. Indeed, its N-terminal part is then released from the membrane of the ER, is translocated to the nucleus where it activates the transcription of their target genes of the ERSE [58].

In 2007, we showed for the first time a specific involvement of ATF6 in cells expressing F508del-CFTR and we demonstrated that when ATF6 expression is decreased by siRNA, the Cl flux through F508del-CFTR are increased [42]. Therefore, the aim of the present work was to show that this effect can be achieved by the use of chemical compounds. The serine protease inhibitor 4-(2-aminoethyl)benzenesulfonyl fluoride (AEBSF) was shown to inhibit the proteolysis of ATF6, leading to the inhibition of the transcriptional of ATF6-target genes [69]. This inhibited ATF6 activation was further shown to be due to a direct S1P inhibition [69]. Therefore, we used AEBSF to treat cells expressing Wt-CFTR and F508del-CFTR. No obvious cell toxicity was observed in the used concentration. We assessed the effect of the compound on BiP and S1P expression, and upon ATF6 expression. We observed an effective UPR inhibition which was further correlated to an increased function of F508del-CFTR in treated cells, in link with a higher amount of the mutated protein within membranes. To further confirm this finding regarding the effect of the S1P blockage upon CFTR, we used another compound know to inhibit S1P. This compound was PF-429242 which, beside its anti-viral activity, is known to inhibit the processing of the activation of ATF6 in response to ER stress [78]. As for AEBSF, no obvious cell toxicity was observed.

Having shown that AEBSF reduced the expression of the cleaved form of ATF6 and decreases S1P expression, we tested the effect of both AEBSF and PF-429242 upon F508del-CFTR's function, using whole cell patch-clamp experiments [82]. For both compounds we showed increased CL efflux in cells expressing F508del-CFTR. This increased F508del-CFTR's function could be explained by an increased expression, an increased translocation towards the membrane, a decreased degradation by ERAD, a decreased recycling or by an increased time of presence and thus membrane localization of the channel. We did not test experimentally all these hypotheses but assessed a potential increased localization of F508del-CFTR within membranes, after treatment. Our results showed that AEBSF and PF-429242 both increase the presence of F508del-CFTR within membranes. Indeed, the appearance after treatment of the cells, of the 170 kDa form of CFTR, which is fully glycosylated, likely indicated that the localization of the protein was increased in membranes or that its maturation was increased (or both). Nevertheless, other hypotheses were not excluded.

In order to depict the molecular action linking AEBSF to the increased function of F508del-CFTR, we performed 2-DE and MS analysis of differentially expressed proteins after treatment. We found that HNRNPH1 and HNRH3 were decreased and that PDIA3 (Grp58), HSP7C, GRP75 and HSP71 were increased, when the cleavage of ATF6 is inhibited. We further performed a bibliographic analysis to characterize these proteins.

From transcription in the nucleus to the cytoplasm, mRNAs associate with proteins (RNA-binding proteins). These interactions with ribonucleoproteins (RNPs) are involved in pre-mRNA processing, transport, localization, translation and stability of mRNAs. Among RNPs, heterogeneous nuclear RNPs (hnRNPs) are proteins that bind to nascent transcripts produced by RNA polymerase II (for review [83]). A specific feature of the hnRNPs is that they undergo nucleocytoplasmic shuttling and that their function involves interactions within many other proteins[83;84]. The H family of hnRNPs includes H1 (H), H2 (H') and H3 hnRNPs which have very similar sequences and which are well known regulators of alternative splicing [85]. Due to their involvement in the regulation of gene expression, hnRNPs have been linked to numerous diseases [86]. We found here that the expression of HNRNPH1 and HNRH3 is decreased in cells when ATF6 cleavage is inhibited. Therefore, a modulation of mRNA processing and alternative splicing may occur. Knowing that post-transcriptional processing of CFTR mRNA may be modulated, leading to an in-frame skipping of exon 9 [87], HNRNPH1 and HNRH3 are possibly involved in modulation of the expression of functional mRNA of F508del-CFTR. Indeed, whereas HNRNPH1 was shown to inhibit alternative splicing in neurons [88], HNRH3 was shown to shown to enhance RNA splicing and processing [89]. HNRNPH1 and HNRH3 are therefore involved in our treated cells but in view of the bibliography it is not clear if they can explain the observed Cl⁻ channel function of F508del-CFTR when ATF6 cleavage is inhibited. They can furthermore be implicated in the maturation of many mRNAs and have an indirect implication upon CFTR maturation and membrane targeting.

PDIA3 (Grp58), HSP7C, GRP75 and HSP71 were increased when ATF6 cleavage was inhibited. The protein PDIA3 (Protein disulfide isomerase A3, Grp58) belongs to the protein disulfide isomerase family, whose members are mainly present, in the ER [90] where it exhibits a stress-responsive protein function. As such, it was identified together with GRP78 and GRP94 with an increased expression after glucose depletion [91]. The main function of PDIA3 (Grp58) is to oxidize thiols and reduce disulfide bonds of proteins, in order to reshuffle improperly formed disulfide bonds and to correct the folding of proteins within the ER [92]. As a chaperone protein [92] and together with calnexin and calreticulin, it is involved in the correct folding of glycoproteins within the ER [93]. Therefore its increased expression after ATF6 inhibition likely favours the refolding of F508del-CFTR, explaining why we found an increased function and an increased amount of the mature form of CFTR in treated cells. Furthermore, PDIA3 was shown to be present in CFTR's protein complex and up-regulated when F508del-CFTR is chemically or genetically rescued [94]. This latest point indicates that we succeeded to rescue F508del-CFTR, as shown by the present results.

HSP71 (71 kDa heat shock protein, HspA1A/HspA1B) belongs to the 70 kDa heat shock protein (HSP70s) family. It is found in cytosol, nucleus, membranes and in extracellular exosomes. It can be induces by stress such as thermal stress, infections, inflammation and oxidants [95]. To fulfill their numerous cellular and stress-induced functions, HSP70s bind ATP [96] and act as unfolding machines able to shift polypeptides to various folding states. When exposed to stressors, HSP70s bind misfolded proteins and prevent their aggregation [97]. Indeed, they HSP70s possess an unfoldase activity since they are able to recognize misfolded and aggregated proteins and to unfold them to a natively refoldable state [98]. Among HSP70s, HspA1A and HspA1B, which only differ by two amino acids, are the major stress-inducible HSP70s [95] with a pivotal role in the protein quality control system of misfolded proteins and in their targeting to degradation [99]. Regarding CFTR, Hsp70 are of main importance. They associate with both Wt-CFTR and F508del-CFTR and dissociate from Wt-CFTR when it is transported from the ER to the Golgi [100]. F508-CFTR/ Hsp70 forms a stable complex permitting the degradation of F508del-CFTR in the pre-Golgi, nonlysosomal, compartments [100]. They are therefore involved in the maturation and in the degradation of unfolded CFTR such as F508del-CFTR. We observed an increased expression of the HSP71 member of HSP70s when ATF6 is inhibited. We thus hypothesize that this increased protein expression is eliminating unfoldable F508del-CFTR and is favouring the maturation and refolding of some reversely unfolded F508del-CFTR. The ultimate effect is likely an increased refolding, as seen in the present results.

Among HSP70s, we also observed an increased expression of HSP7C (Hsc70; constitutive) which is also known as HspA8 [97]. HspA8 is a cognate Hsp70 family with essentially folding and transport of polypeptides across intracellular membranes as main functions [97]. Interestingly, stress maintains HSPA8 in a monomeric form leading to the release of unfolded proteins previously bound to it [101]. Indeed, HSPA8 has four main functions: 1) it binds native and misfolded proteins to favor their refolding [102], 2) it transports unfolded proteins through membranes to deliver them to their final localization [103], 3) it recruits proteins for proteasome activation [104], and 4) it brings proteins to the endosomes and triggers autophagy [105]. It forms a cytosolic complex together with CHIP E3 and cooperates with the ER membrane associated ubiquitin ligase complex to favour triage of proteins [106]. HSP7C, together with Hsp70, is involved in the proper folding of CFTR [106] by direct interactions with a higher affinity for F508del-CFTR than for Both Wt-CFTR [107]. Thus, it's over expression in the present work is in favour of a greater folding and exportation of F508del-CFTR to the membrane.

GRP75 (Glucose-regulated protein 75), also called mortalin (sometimes termed GRP75/mtHSP70/PBP74), is a member of the HSP70s family [108]. Mortalin is translated in the cytoplasm and is transported into mitochondria [109]. Nevertheless, it is also found in the ER endoplasmic reticulum, and in the cytosol [110]. Mortalin is a stress response protein and its increased expression is associated with cellular protection, as it permits cells to survive lethal conditions [111, 112]. It has a broad panel of functions such as stress response, intracellular trafficking, cell differentiation and proliferation (for review [113]). Because it ensures the final localization of proteins, modifies their functions, protect them against stress and is up-regulated when F508del-CFTR is rescued [94, 114, 115], its overexpression when ATF6 is inhibited likely leads to the recovery of some mutated CFTR, explaining our present results.

The protein network in which a protein takes place is a good indicator of the pathway in which it is involved. Thus, we search for interacting proteins with PDIA3 (Grp58), HSP7C, GRP75 and HSP7, using STRING which is a global resource currently covering 9,643,763 proteins. In an unexpected way, we found that all the proteins that were found modulated when ATF6 is inhibited have a common partner: ubiquitin C (UBC). This result was further confirmed by the analysis of the relevant bibliography for each interaction (HNRNPH1-UBC, [116]; HNRH3-UBC, [117]; PDIA3 (Grp58)-UBC, [118]; HSP7C-HSP71- and GRP75-UBC, [119]). Unfolded proteins in the ER are exported into the cytosol and degraded via the ubiquitin-proteasome pathway, a process termed ER-associated degradation (ERAD). Therefore, protein ubiquitylation contributes to the regulation of protein degradation. As any protein, both Wt- and F508del-CFTR undergo ubiquitination and degradation [120]. Misfolding of F508del-CFTR facilitates its lysosomal targeting by promoting its ubiquitination [121]. Therefore, if UBC is overexpressed in our model, what we do not know, it would not explain the higher amount of F508del-CFTR in cell membranes when ATF6 is inhibited. Nevertheless, the promoter of the UBC gene (UBC) contains putative heat shock elements (HSEs) which mediate UBC induction upon stress. At least three HSEs, exist in the UBC promoter: two distal, and one proximal to the transcription start site, all bound by transcription factors belonging to the heat shock factor (HSF) family. The proximal is a negative regulator of the stress-induced transcription [122]. Therefore, if a HSE with a negative role on the transcription is overexpressed, it could explain why in our hands, more F508del-CFTR is present in the membrane. It has also to be noticed that we recently showed a pivotal role of UBC as a modifier gene in CF by in silico studies [123].

CONCLUSION

We showed that the inhibition of the cleavage of ATF6 by S1P alleviates the defects observed in the membrane localization and Cl— channel function of F508del-CFTR. Accordingly, inhibitors of S1P are suitable for the treatment of diseases associated with reduced CFTR function.

REFERENCES

Throughout this application, various references describe the state of the art to which this invention pertains. The disclosures of these references are hereby incorporated by reference into the present disclosure.

[1] J. R. Riordan, J. M. Rommens, B. Kerem, N. Alon, R. Rozmahel, Z. Grzelczak, J. Zielenski, S. Lok, N. Playsic, J. L. Chou, et al., Identification of the cystic fibrosis gene: cloning and characterization of complementary DNA, Science (New York, N.Y., 245 (1989) 1066-1073.

[2] M. P. Anderson, R. J. Gregory, S. Thompson, D. W. Souza, S. Paul, R. C. Mulligan, A. E. Smith, M. J. Welsh, Demonstration that CFTR is a chloride channel by alteration of its anion selectivity, Science (New York, N.Y., 253 (1991) 202-205.

[3] D. P. Rich, M. P. Anderson, R. J. Gregory, S. H. Cheng, S. Paul, D. M. Jefferson, J. D. McCann, K. W. Klinger, A. E. Smith, M. J. Welsh, Expression of cystic fibrosis transmembrane conductance regulator corrects defective chloride channel regulation in cystic fibrosis airway epithelial cells, Nature, 347 (1990) 358-363.

[4] M. J. Gething, J. Sambrook, Protein folding in the cell, Nature, 355 (1992) 33-45.

[5] K. Araki, K. Nagata, Protein folding and quality control in the ER, Cold Spring Harb Perspect Biol, 4 (2012) a015438.

[6] A. Ruggiano, O. Foresti, P. Carvalho, Quality control: ER-associated degradation: protein quality control and beyond, The Journal of cell biology, 204 (2014) 869-879.

[7] R. J. Kaufman, Stress signaling from the lumen of the endoplasmic reticulum: coordination of gene transcriptional and translational controls, Genes & development, 13 (1999) 1211-1233.

[8] C. Y. Liu, R. J. Kaufman, The unfolded protein response, Journal of cell science, 116 (2003) 1861-1862.

[9] K. Mori, Tripartite management of unfolded proteins in the endoplasmic reticulum, Cell, 101 (2000) 451-454.

[10] D. Ron, P. Walter, Signal integration in the endoplasmic reticulum unfolded protein response, Nature reviews, 8 (2007) 519-529.

[11] M. Schroder, R. J. Kaufman, ER stress and the unfolded protein response, Mutation research, 569 (2005) 29-63.

[12] R. Casagrande, P. Stern, M. Diehn, C. Shamu, M. Osario, M. Zuniga, P. O. Brown, H. Ploegh, Degradation of proteins from the ER of S. cerevisiae requires an intact unfolded protein response pathway, Molecular cell, 5 (2000) 729-735.

[13] R. Friedlander, E. Jarosch, J. Urban, C. Volkwein, T. Sommer, A regulatory link between ER-associated protein degradation and the unfolded-protein response, Nature cell biology, 2 (2000) 379-384.

[14] B. Meusser, C. Hirsch, E. Jarosch, T. Sommer, ERAD: the long road to destruction, Nature cell biology, 7 (2005) 766-772.

[15] S. Oyadomari, C. Yun, E. A. Fisher, N. Kreglinger, G. Kreibich, M. Oyadomari, H. P. Harding, A. G. Goodman, H. Harant, J. L. Garrison, J. Taunton, M. G. Katze, D. Ron, Cotranslocational degradation protects the stressed endoplasmic reticulum from protein overload, Cell, 126 (2006) 727-739.

[16] K. J. Travers, C. K. Patil, L. Wodicka, D. J. Lockhart, J. S. Weissman, P. Walter, Functional and genomic analyses reveal an essential coordination between the unfolded protein response and ER-associated degradation, Cell, 101 (2000) 249-258.

[17] M. Schroder, R. J. Kaufman, The mammalian unfolded protein response, Annual review of biochemistry, 74 (2005) 739-789.

[18] D. Scheuner, B. Song, E. McEwen, C. Liu, R. Laybutt, P. Gillespie, T. Saunders, S. Bonner-Weir, R. J. Kaufman, Translational control is required for the unfolded protein response and in vivo glucose homeostasis, Molecular cell, 7 (2001) 1165-1176.

[19] M. E. Martino, J. C. Olsen, N. B. Fulcher, M. C. Wolfgang, W. K. O'Neal, C. M. Ribeiro, Airway epithelial inflammation-induced endoplasmic reticulum Ca2+ store expansion is mediated by X-box binding protein-1, J Biol Chem, 284 (2009) 14904-14913.

[20] C. M. Ribeiro, W. K. O'Neal, Endoplasmic reticulum stress in chronic obstructive lung diseases, Current molecular medicine, 12 (2012) 872-882.

[21] E. F. van't Wout, A. van Schadewijk, R. van Boxtel, L. E. Dalton, H. J. Clarke, J. Tommassen, S. J. Marciniak, P. S. Hiemstra, Virulence Factors of *Pseudomonas aeruginosa* Induce Both the Unfolded Protein and Integrated Stress Responses in Airway Epithelial Cells, PLoS pathogens, 11 (2015) e1004946.

[22] J. Celli, R. M. Tsolis, Bacteria, the endoplasmic reticulum and the unfolded protein response: friends or foes?, Nature reviews, 13 (2015) 71-82.

[23] R. V. Rao, S. Castro-Obregon, H. Frankowski, M. Schuler, V. Stoka, G. del Rio, D. E. Bredesen, H. M. Ellerby, Coupling endoplasmic reticulum stress to the cell death program. An Apaf-1-independent intrinsic pathway, J Biol Chem, 277 (2002) 21836-21842.

[24] C. Xu, B. Bailly-Maitre, J. C. Reed, Endoplasmic reticulum stress: cell life and death decisions, The Journal of clinical investigation, 115 (2005) 2656-2664.

[25] I. G. Haas, M. Wabl, Immunoglobulin heavy chain binding protein, Nature, 306 (1983) 387-389.

[26] J. A. Morris, A. J. Dorner, C. A. Edwards, L. M. Hendershot, R. J. Kaufman, Immunoglobulin binding protein (BiP) function is required to protect cells from endoplasmic reticulum stress but is not required for the secretion of selective proteins, J Biol Chem, 272 (1997) 4327-4334.

[27] S. Munro, H. R. Pelham, An Hsp70-like protein in the ER: identity with the 78 kd glucose-regulated protein and immunoglobulin heavy chain binding protein, Cell, 46 (1986) 291-300.

[28] R. P. Shiu, J. Pouyssegur, I. Pastan, Glucose depletion accounts for the induction of two transformation-sensitive membrane proteinsin Rous sarcoma virus-transformed chick embryo fibroblasts, Proc Natl Acad Sci USA, 74 (1977) 3840-3844.

[29] K. Kohno, How transmembrane proteins sense endoplasmic reticulum stress, Antioxidants & redox signaling, 9 (2007) 2295-2303.

[30] Y. Shi, K. M. Vattem, R. Sood, J. An, J. Liang, L. Stramm, R. C. Wek, Identification and characterization of pancreatic eukaryotic initiation factor 2 alpha-subunit kinase, PEK, involved in translational control, Molecular and cellular biology, 18 (1998) 7499-7509.

[31] J. S. Cox, C. E. Shamu, P. Walter, Transcriptional induction of genes encoding endoplasmic reticulum resident proteins requires a transmembrane protein kinase, Cell, 73 (1993) 1197-1206.

[32] C. Zhu, F. E. Johansen, R. Prywes, Interaction of ATF6 and serum response factor, Molecular and cellular biology, 17 (1997) 4957-4966.

[33] H. P. Harding, H. Calfon, F. Urano, I. Novoa, D. Ron, Transcriptional and translational control in the Mammalian unfolded protein response, Annual review of cell and developmental biology, 18 (2002) 575-599.

[34] A. Bertolotti, Y. Zhang, L. M. Hendershot, H. P. Harding, D. Ron, Dynamic interaction of BiP and ER stress transducers in the unfolded-protein response, Nature cell biology, 2 (2000) 326-332.

[35] J. Shen, E. L. Snapp, J. Lippincott-Schwartz, R. Prywes, Stable binding of ATF6 to BiP in the endoplasmic reticulum stress response, Molecular and cellular biology, 25 (2005) 921-932.

[36] J. Shen, X. Chen, L. Hendershot, R. Prywes, ER stress regulation of ATF6 localization by dissociation of BiP/GRP78 binding and unmasking of Golgi localization signals, Developmental cell, 3 (2002) 99-111.

[37] K. Ma, K. M. Vattem, R. C. Wek, Dimerization and release of molecular chaperone inhibition facilitate activation of eukaryotic initiation factor-2 kinase in response to endoplasmic reticulum stress, J Biol Chem, 277 (2002) 18728-18735.

[38] Y. Wang, J. Shen, N. Arenzana, W. Tirasophon, R. J. Kaufman, R. Prywes, Activation of ATF6 and an ATF6 DNA binding site by the endoplasmic reticulum stress response, J Biol Chem, 275 (2000) 27013-27020.

[39] Y. Kozutsumi, M. Segal, K. Normington, M. J. Gething, J. Sambrook, The presence of malfolded proteins in the endoplasmic reticulum signals the induction of glucose-regulated proteins, Nature, 332 (1988) 462-464.

[40] A. S. Lee, The ER chaperone and signaling regulator GRP78/BiP as a monitor of endoplasmic reticulum stress, Methods (San Diego, Calif., 35 (2005) 373-381.

[41] B. Kerem, J. M. Rommens, J. A. Buchanan, D. Markiewicz, T. K. Cox, A. Chakravarti, M. Buchwald, L. C. Tsui, Identification of the cystic fibrosis gene: genetic analysis, Science (New York, N.Y., 245 (1989) 1073-1080.

[42] M. Kerbiriou, M. A. Le Drevo, C. Ferec, P. Trouve, Coupling cystic fibrosis to endoplasmic reticulum stress: Differential role of Grp78 and ATF6, Biochim Biophys Acta, (2007).

[43] R. Bartoszewski, A. Rab, A. Jurkuvenaite, M. Mazur, J. Wakefield, J. F. Collawn, Z. Bebok, Activation of the Unfolded Protein Response by {Delta}F508 CFTR, Am J Respir Cell Mol Biol, (2008).

[44] P. Gomes-Alves, F. Couto, C. Pesquita, A. V. Coelho, D. Penque, Rescue of F508del-CFTR by RXR motif inactivation triggers proteome modulation associated with the unfolded protein response, Biochim Biophys Acta, 1804 (2010) 856-865.

[45] H. L. Pahl, P. A. Baeuerle, A novel signal transduction pathway from the endoplasmic reticulum to the nucleus is mediated by transcription factor NF-kappa B, The EMBO journal, 14 (1995) 2580-2588.

[46] C. J. Blohmke, M. L. Mayer, A. C. Tang, A. F. Hirschfeld, C. D. Fjell, M. A. Sze, R. Falsafi, S. Wang, K. Hsu, M. A. Chilvers, J. C. Hogg, R. E. Hancock, S. E. Turvey, Atypical Activation of the Unfolded Protein Response in Cystic Fibrosis Airway Cells Contributes to p38 MAPK-Mediated Innate Immune Responses, J Immunol, 189 (2012) 5467-5475.

[47] M. Cohen-Cymberknoh, E. Kerem, T. Ferkol, A. Elizur, Airway inflammation in cystic fibrosis: molecular mechanisms and clinical implications, Thorax, 68 (2013) 1157-1162.

[48] A. D. Garg, A. Kaczmarek, O. Krysko, P. Vandenabeele, D. V. Krysko, P. Agostinis, ER stress-induced inflammation: does it aid or impede disease progression?, Trends in molecular medicine, (2012).

[49] K. Zhang, R. J. Kaufman, From endoplasmic-reticulum stress to the inflammatory response, Nature, 454 (2008) 455-462.

[50] K. Zhang, X. Shen, J. Wu, K. Sakaki, T. Saunders, D. T. Rutkowski, S. H. Back, R. J. Kaufman, Endoplasmic reticulum stress activates cleavage of CREBH to induce a systemic inflammatory response, Cell, 124 (2006) 587-599.

[51] A. J. Weber, G. Soong, R. Bryan, S. Saba, A. Prince, Activation of NF-kappaB in airway epithelial cells is dependent on CFTR trafficking and Cl— channel function, Am J Physiol Lung Cell Mol Physiol, 281 (2001) L71-78.

[52] A. Rab, R. Bartoszewski, A. Jurkuvenaite, J. Wakefield, J. F. Collawn, Z. Bebok, Endoplasmic reticulum stress and the unfolded protein response regulate genomic cystic fibrosis transmembrane conductance regulator expression, Am J Physiol Cell Physiol, 292 (2007) C756-766.

[53] Bebok Z, Collawn J F, Wakefield J, Parker W, Li Y, Varga K, Sorscher E J, Clancy J P. Failure of cAMP agonists to activate rescued ΔF508 CFTR in CFBE41o– airway epithelial monolayers. J Physiol. 2005; 569:601-615.

[54] X. Chen, J. Shen, R. Prywes, The luminal domain of ATF6 senses endoplasmic reticulum (ER) stress and causes translocation of ATF6 from the ER to the Golgi, J Biol Chem, 277 (2002) 13045-13052.

[55] K. Haze, H. Yoshida, H. Yanagi, T. Yura, K. Mori, Mammalian transcription factor ATF6 is synthesized as a transmembrane protein and activated by proteolysis in response to endoplasmic reticulum stress, Mol Biol Cell, 10 (1999) 3787-3799.

[56] J. Shen, R. Prywes, ER stress signaling by regulated proteolysis of ATF6, Methods (San Diego, Calif., 35 (2005) 382-389.

[57] J. Ye, R. B. Rawson, R. Komuro, X. Chen, U. P. Dave, R. Prywes, M. S. Brown, J. L. Goldstein, ER stress induces cleavage of membrane-bound ATF6 by the same proteases that process SREBPs, Molecular cell, 6 (2000) 1355-1364.

[58] K. Yamamoto, H. Yoshida, K. Kokame, R. J. Kaufman, K. Mori, Differential contributions of ATF6 and XBP1 to the activation of endoplasmic reticulum stress-responsive cis-acting elements ERSE, UPRE and ERSE-II, Journal of biochemistry, 136 (2004) 343-350.

[59] K. Yamamoto, T. Sato, T. Matsui, M. Sato, T. Okada, H. Yoshida, A. Harada, K. Mori, Transcriptional induction of mammalian ER quality control proteins is mediated by single or combined action of ATF6alpha and XBP1, Developmental cell, 13 (2007) 365-376.

[60] J. Wu, D. T. Rutkowski, M. Dubois, J. Swathirajan, T. Saunders, J. Wang, B. Song, G. D. Yau, R. J. Kaufman, ATF6alpha optimizes long-term endoplasmic reticulum function to protect cells from chronic stress, Developmental cell, 13 (2007) 351-364.

[61] Y. Adachi, K. Yamamoto, T. Okada, H. Yoshida, A. Harada, K. Mori, ATF6 is a transcription factor specializing in the regulation of quality control proteins in the endoplasmic reticulum, Cell Struct Funct, 33 (2008) 75-89.

[62] F. Damiano, R. Tocci, G. V. Gnoni, L. Siculella, Expression of citrate carrier gene is activated by ER stress effectors XBP1 and ATF6alpha, binding to an UPRE in its promoter, Biochim Biophys Acta, 1849 (2015) 23-31.

[63] A. H. Lee, E. F. Scapa, D. E. Cohen, L. H. Glimcher, Regulation of hepatic lipogenesis by the transcription factor XBP1, Science (New York, N.Y., 320 (2008) 1492-1496.

[64] L. H. Glimcher, XBP1: the last two decades, Annals of the rheumatic diseases, 69 Suppl 1 (2010) i67-71.

[65] I. Kim, W. Xu, J. C. Reed, Cell death and endoplasmic reticulum stress: disease relevance and therapeutic opportunities, Nat Rev Drug Discov, 7 (2008) 1013-1030.

[66] S. Oyadomari, M. Mori, Roles of CHOP/GADD153 in endoplasmic reticulum stress, Cell Death Differ, 11 (2004) 381-389.

[67] H. P. Harding, Y. Zhang, A. Bertolotti, H. Zeng, D. Ron, Perk is essential for translational regulation and cell survival during the unfolded protein response, Molecular cell, 5 (2000) 897-904.

[68] T. Namba, T. Ishihara, K. Tanaka, T. Hoshino, T. Mizushima, Transcriptional activation of ATF6 by endoplasmic reticulum stressors, Biochemical and biophysical research communications, 355 (2007) 543-548.

[69] T. Okada, K. Haze, S. Nadanaka, H. Yoshida, N. G. Seidah, Y. Hirano, R. Sato, M. Negishi, K. Mori, A serine protease inhibitor prevents endoplasmic reticulum stress-induced cleavage but not transport of the membrane-bound transcription factor ATF6, J Biol Chem, 278 (2003) 31024-31032.

[70] E. Bruscia, F. Sangiuolo, P. Sinibaldi, K. K. Goncz, G. Novelli, D. C. Gruenert, Isolation of CF cell lines corrected at DeltaF508-CFTR locus by SFHR-mediated targeting, Gene Ther, 9 (2002) 683-685.

[71] K. Kunzelmann, E. M. Schwiebert, P. L. Zeitlin, W. L. Kuo, B. A. Stanton, D. C. Gruenert, An immortalized cystic fibrosis tracheal epithelial cell line homozygous for the delta F508 CFTR mutation, Am J Respir Cell Mol Biol, 8 (1993) 522-529.

[72] B. Illek, R. Maurisse, L. Wahler, K. Kunzelmann, H. Fischer, D. C. Gruenert, Cl transport in complemented CF bronchial epithelial cells correlates with CFTR mRNA expression levels, Cell Physiol Biochem, 22 (2008) 57-68.

[73] O. H. Lowry, N. J. Rosebrough, A. L. Farr, R. J. Randall, Protein measurement with the Folin phenol reagent, J Biol Chem, 193 (1951) 265-275.

[74] C. Farre, S. Stoelzle, C. Haarmann, M. George, A. Bruggemann, N. Fertig, Automated ion channel screening: patch clamping made easy, Expert opinion on therapeutic targets, 11 (2007) 557-565.

[75] N. Benz, S. Le Hir, C. Norez, M. Kerbiriou, M. L. Calvez, F. Becq, P. Trouve, C. Ferec, Improvement of chloride transport defect by gonadotropin-releasing hormone (GnRH) in cystic fibrosis epithelial cells, PLoS ONE, 9 (2014) e88964.

[76] G. W. Carlile, R. Robert, D. Zhang, K. A. Teske, Y. Luo, J. W. Hanrahan, et al. Correctors of protein trafficking defects identified by a novel high-throughput screening assay, ChemBioChem, 8 (2007) 1012-1020.

[77] F. Huguet, M. L. Calvez, N. Benz, S. Le Hir, O. Mignen, P. Buscaglia, F. D. Horgen, C. Férec, M. Kerbiriou, P. Trouvé. Function and regulation of TRPM7, as well as intracellular magnesium content, are altered in cells expressing DF508-CFTR and G551D-CFTR. Cellular and Molecular Life Sciences, 73 (2016) (17):3351-73.

[78] A. Pasquatoa, C. Rochata, D. J. Burria, G. Pasquala, J. C. de la Torreb, S. Kunza. Evaluation of the anti-arenaviral activity of the subtilisin kexin isozyme-1/site-1 protease inhibitor PF-429242. Virology, 423 (2012) 14-22.

[79] C. M. Farinha, M. Sousa, S. Canato, A. Schmidt, I. Uliyakina, M. D. Amaral. Increased efficacy of VX-809 in different cellular systems results from an early stabilization effect of F508del-CFTR. Pharmacol Res Perspect. (3) 2015 (4):e00152.

[80] D. Szklarczyk, A. Franceschini, S. Wyder, K. Forslund, D. Heller, J. Huerta-Cepas et al. STRING v10: protein-protein interaction networks, integrated over the tree of life. Nucleic Acids Res. 43 (2015) D447-52.

[81] J. Shang. Quantitative measurement of events in the mammalian unfolded protein response. Methods, 35 (2005) 390-394.3.

[82] F. Huguet, M. L. Calvez, N. Benz, S. Le Hir, O. Mignen, P. Buscaglia, F. D. Horgen, C. Férec, M. Kerbiriou and P. Trouvé. Function and regulation of TRPM7, as well as intracellular magnesium content, are altered in cells expressing DF508-CFTR and G551D-CFTR. Cellular and Molecular Life Sciences, 73 (2016) (17)3351-73.

[83] S. P. Han, Y. H. Tang, R. Smith. Functional diversity of the hnRNPs: past, present and perspectives. Biochemical Journal 430 (2010) (3)379-392.

[84] S. Pinol-Roma, G. Dreyfuss. Shuttling of pre-mRNA binding proteins between nucleus and cytoplasm. Nature 355 (1992) 730-732.

[85] R. Martinez-Contreras, J. F. Fisette, F. H. Nasim, R. Madden, M. Cordeau, B. Chabot. Intronic binding sites for hnRNP A/B and hnRNP F/H proteins stimulate pre-mRNA splicing. PLoS Biol. 4(2006) 172-185.

[86] B. Carpenter, C. MacKay, A. Alnabulsi, M. MacKay, C. Telfer, W. T. Melvin, G. I. Murray. The roles of heterogeneous nuclear ribonucleoproteins in tumour development and progression. Biochim. Biophys. Acta 1765 (2006) 85-100.

[87] C. S. Chu, B. C. Trapnell, S. Curristin, G. R. Cutting, R. G. Crystal. Genetic basis of variable exon 9 skipping in cystic fibrosis transmembrane conductance regulator mRNA. Nature Genet. 3 (1993) 151-156.

[88] I. Grammatikakis, P. Zhang, A. C. Panda, J. Kim, S. Maudsley, K. Abdelmohsen, X. Yang, J. L. Martindale, O. Motino, E. R. Hutchison, M. P. Mattson, M. Gorospe. Alternative splicing of neuronal differentiation factor TRF2 regulated by HNRNPH1/H2. Cell Rep. 15 (2016) 926-934.

[89] D. Mahé, P. Mähl, R. Gattoni, N. Fischer, M. G. Mattei§., J. Stévenin, J. P. Fuchs Cloning of Human 2H9 Heterogeneous Nuclear Ribonucleoproteins. The Journal of Biological Chemistry 272 (1997) 1827-1836.

[90] C. Turano, S. Coppari, F. Altieri, A. Ferraro. Proteins of the PDI family: unpredicted non-ER locations and functions. J. Cell. Physiol. 193 (2002) 154-163.

[91] A. S. Lee. The accumulation of three specific proteins related to glucose regulated proteins in a temperature-sensitive hamster mutant cell line K12. J. Cell. Physiol. 106 (1981) 119-125.

[92] R. B. Freedman, T. R. Hirst, M. F. Tuite. Protein disulphide isomerase: building bridges in protein folding. Trends Biochem. Sci. 19 (1994) 331-336.

[93] J. G. Elliott, J. D. Oliver, S. High. The thiol-dependent reductase ERp57 interacts specifically with N-glycosylated integral membrane proteins. J Biol Chem 272 (1997) 13849-13855.

[94] O. V. Singh, H. B. Pollard, P. L. Zeitlin. Chemical Rescue of ΔF508-CFTR Mimics Genetic Repair in Cystic Fibrosis Bronchial Epithelial Cells. Mol Cell Proteomics. 7 (2008) (6): 1099-1110.

[95] S. Lindquist, E. A. Craig. The heat-shock proteins. Annu Rev Genet. 22 (1988) 631-677.

[96] R. P. De Los, P. Goloubinoff. Hsp70 chaperones use ATP to remodel native protein oligomers and stable aggregates by entropic pulling. Nat Struct Mol Biol 23 (2016) 766-769.

[97] Radons J. The human HSP70 family of chaperones: where do we stand? Cell Stress Chaperones 21 (2016) 379-404.

[98] S. K. Sharma, R. P. De Los, P. Christen, A. Lustig, P. Goloubinoff. The kinetic parameters and energy cost of the Hsp70 chaperone as a polypeptide unfoldase. Nat Chem Biol. 6 (2010) 914-920.

[99] S. Canal, S. Alberti, P. A. Arrigo, J. L. Benesch, I. J. Benjamin, W. Boelens, B. Bartelt-Kirbach, B. J. J. M. Brundel, J. Buchner. The growing world of small heat shock proteins: from structure to functions. Cell Stress and Chaperones (2017). doi:10.1007/s12192-017-0787-8.

[100] Y. Yang, S. Janich, J. A. Cohn, J. M. Wilson. The common variant of cystic fibrosis transmembrane conductance regulator is recognized by hsp70 and degraded in a pre-Golgi nonlysosomal compartment. Proc Natl Acad Sci USA 90 (1993) 9480-9484.

[101] E. R. Zuiderweg, L. E. Hightower, J. E. Gestwicki. The remarkable multivalency of the Hsp70 chaperones. Cell Stress Chaperones. 22 (2017) 173-189.

[102] J. C. Young, V. R. Agashe, K. Siegers, F. U. Hartl. Pathways of chaperone-mediated protein folding in the cytosol. Nat Rev Mol Cell Biol 5 (2004) 781-791.

[103] J. Hohfeld, F. U. Hartl. Post-translational protein import and folding. Curr Opin Cell Biol 6 (1994) 499-509.

[104] J. Demand, J. Luders, J. Hohfeld. The carboxy-terminal domain of Hsc70 provides binding sites for a distinct set of chaperone cofactors. Mol Cell Biol 18 (1998) 2023-2028.

[105] A. E. Majeski, J. F. Dice. Mechanisms of chaperone-mediated autophagy. Int J Biochem Cell Biol 36 (2004) 2435-2444.

[106] J. M. Younger, H. Y. Ren, L. Chen, C. Y. Fan, A. Fields, C. Patterson, D. M. Cyr. A foldable CFTR{Delta}F508 biogenic intermediate accumulates upon inhibition of the Hsc70-CHIP E3 ubiquitin ligase. J. Cell Biol. 167 (2004) 1075-1085.

[107] M. D. Amaral. CFTR and chaperones: processing and degradation. J Mol Neurosci 23 (2004) 41-48.

[108] T. J. Webster, D. J. Naylor, D. J. Hartman, P. B. Hoj, N. J. Hoogenraad. cDNA cloning and efficient mitochondrial import of pre-mtHSP70 from rat liver. DNA Cell Biol. 13 (1994) 1213-1220.

[109] R. Wadhwa, K. Taira, S. C. Kaul. An Hsp70 family chaperone, mortalin/mthsp70/PBP74/Grp75: What, when, and where? Cell Stress Chaperones. 581 (2002) 3702-3710.

[110] Q. Ran, R. Wadhwa, R. Kawai, S. C. Kaul, R. N. Sifers, R. J. Bick, J. R. Smith, O. M. Pereira-Smith. Extramitochondrial localization of mortalin/mthsp70/PBP74/GRP75. Biochem. Biophys. Res. Commun. 275 (2000) 174-179.

[111] M. Qu, Z. Zhou, S. Xu, C. Chen, Z. Yu, D. Wang. Mortalin overexpression attenuates beta-amyloid-induced neurotoxicity in SH-SY5Y cells. Brain Res. 1368 (2011) 336-345.

[112] L. Xu, L. A. Voloboueva, Y. Ouyang, J. F. Emery, R. G. Giffard. Overexpression of mitochondrial Hsp70/Hsp75 in rat brain protects mitochondria, reduces oxidative stress, and protects from focal ischemia. J. Cereb. Blood Flow Metab. 29 (2009) 365-374.

[113] P. R. Dores-Silva, L. R. S. Barbosa, C. H. I. Ramos, J. C. Borges. Human Mitochondrial Hsp70 (Mortalin): Shedding Light on ATPase Activity, Interaction with Adenosine Nucleotides, Solution Structure and Domain Organization. PLoS One 10(1) (2015) e0117170.

[114] S. Taurin, V. Seyrantepe, S. N. Orlov, T. L. Tremblay, P. Thibault, M. R. Bennett, P. Hamet, A. V. Pshezhetsky. Proteome analysis and functional expression identify mortalin as an antiapoptotic gene induced by elevation of [Na+]i/[K+]i ratio in cultured vascular smooth muscle cells. Circ. Res., 91 (2002) 915-922.

[115] S. C. Kaul, C. C. Deocaris, R. Wadhwa. Three faces of mortalin: A housekeeper, guardian and killer. Experimental Gerontology 42 (2007) 263-274.

[116] F. Lopitz-Otsoa, E. Rodriguez-Suarez, F. Aillet, J. Casado-Vela, V. Lang, R. Matthiesen, F. Elortza, M. S. Rodriguez. Integrative analysis of the ubiquitin proteome isolated using Tandem Ubiquitin Binding Entities (TUBEs). J Proteomics. 75(10) (2012) 2998-3014.

[117] J. M. Danielsen, K. B. Sylvestersen, S. Bekker-Jensen, D. Szklarczyk, J. W. Poulsen, H. Horn, L. J. Jensen, N. Mailand, M. L. Nielsen. Mass spectrometric analysis of lysine ubiquitylation reveals promiscuity at site level. Mol Cell Proteomics. 10(3) (2011) M110.003590.

[118] T. Gururaja, W. Li, W. S. Noble, D. G. Payan, D. C. Anderson. Multiple functional categories of proteins identified in an in vitro cellular ubiquitin affinity extract using shotgun peptide sequencing. J Proteome Res. 2(4) (2003) 394-404.

[119] K. Xiao, D. B. McClatchy, A. K. Shukla, Y. Zhao, M. Chen, S. K. Shenoy, J. R. Yates, R. J. Lefkowitz. Functional specialization of beta-arrestin interactions revealed by proteomic analysis. Proc Natl Acad Sci USA. 104(29) (2007) 12011-12016.

[120] C. L. Ward, S. Omura, R. R. Kopito. Degradation of CFTR by the ubiquitin-proteasome pathway. Cell. 83(1) (1995) 121-7.

[121] M. Sharma, F. Pampinella, C. Nemes, M. Benharouga, J. So, K. Du, K. G. Bache, B. Papsin, N. Zerangue, H. Stenmark, G. L. Lukacs. Misfolding diverts CFTR from recycling to degradation: quality control at early endosomes. J Cell Biol. 164(6) (2004) 923-33.

[122] R. Crinelli, M. Bianchi, L. Radici, E. Carloni, E. Giacomini, M. Magnani. Molecular Dissection of the Human Ubiquitin C Promoter Reveals Heat Shock Element Architectures with Activating and Repressive Functions. PLoS One. 10(8) (2015) e0136882.

[123] P. Trouvé, E. Génin, C. Férec. In silico search for modifier genes associated with Pancreatic and Liver Disease in Cystic Fibrosis. PLoSONE, 12(3) (2017) e0173822.

The invention claimed is:

1. A method of treating a disease or symptom associated with reduced Cystic fibrosis transmembrane conductance regulator (CFTR) function in a subject in need thereof comprising administering to the subject having the disease or symptom a therapeutically effective amount of a site 1 protease (S1P) inhibitor,
wherein the disease or symptom to be treated is chronic obstructive pulmonary disease (COPD).

2. The method of claim 1, wherein the subject suffers from a disease associated with reduced CFTR function due to a mutation in the gene encoding CFTR or environmental factors.

3. The method of claim 2, wherein the mutation is selected from the group consisting of F508del-CFTR, R117H CFTR, and G551D CFTR.

4. The method of claim 1, wherein the S1P inhibitor is a small organic molecule.

5. The method of claim 1, wherein the S1P inhibitor is the small organic molecule PF-429242 (4-(diethylaminomethyl)-N-[2-(2-methoxyphenyl)ethyl]-N-pyrrolidin-3-yl-benzamide; dihydrochloride).

6. The method of claim 1, wherein the S1P inhibitor is an inhibitor of S1P expression.

7. The method of claim 6, wherein the inhibitor of S1P expression is an antisense oligonucleotide.

8. The method of claim 1, wherein the S1P inhibitor is delivered by any device adapted to introduce one or more therapeutic compositions into the upper and/or lower respiratory tract.

9. The method of claim 1, wherein chronic obstructive pulmonary disease (COPD) is smoke induced COPD or COPD with chronic bronchitis.

10. A method of treating a disease or symptom associated with reduced Cystic fibrosis transmembrane conductance regulator (CFTR) function in a subject in need thereof comprising administering to the subject having the disease or symptom a therapeutically effective amount of a site 1 protease (S1P) inhibitor,
wherein the disease or symptom to be treated is cystic fibrosis.

11. The method of claim 10, wherein the subject suffers from a disease associated with reduced CFTR function due to a mutation in the gene encoding CFTR or environmental factors.

12. The method of claim 11, wherein the mutation is selected from the group consisting of F508del-CFTR, R117H CFTR, and G551D CFTR.

13. The method of claim 10, wherein the S1P inhibitor is a small organic molecule.

14. The method of claim 10, wherein the S1P inhibitor is the small organic molecule PF-429242 (4-(diethylaminomethyl)-N-[2-(2-methoxyphenyl)ethyl]-N-pyrrolidin-3-yl-benzamide; dihydrochloride).

15. The method of claim 10, wherein the S1P inhibitor is an inhibitor of S1P expression.

16. The method of claim 15, wherein the inhibitor of S1P expression is an antisense oligonucleotide.

17. The method of claim 10, wherein the S1P inhibitor is delivered by any device adapted to introduce one or more therapeutic compositions into the upper and/or lower respiratory tract.

* * * * *

UNITED STATES PATENT AND TRADEMARK OFFICE
CERTIFICATE OF CORRECTION

PATENT NO. : 11,458,118 B2
APPLICATION NO. : 16/606236
DATED : October 4, 2022
INVENTOR(S) : Pascal Trouve et al.

Page 1 of 1

It is certified that error appears in the above-identified patent and that said Letters Patent is hereby corrected as shown below:

In the Specification

Column 13,
Line 43, "the currents" should read --the Cl$^-$ currents--.
Line 51, "of the channel" should read --of the Cl$^-$ channel--.

Column 14,
Line 57, "Cl flux" should read --Cl$^-$ flux--.

Column 15,
Line 17, "CL efflux" should read --Cl$^-$ efflux--.
Line 34, "increased function" should read --increased Cl$^-$ function--.

Signed and Sealed this
Fifth Day of September, 2023

Katherine Kelly Vidal
*Director of the United States Patent and Trademark Office*